United States Patent [19]

Hendricks et al.

[11] Patent Number: 5,503,982
[45] Date of Patent: Apr. 2, 1996

[54] DETECTION OF AN ACUTE MYOCARDIAL INFARCTION IN A PATIENT

[75] Inventors: James B. Hendricks; Jawahar L. Mehta, both of Gainsville, Fla.

[73] Assignee: Research Corporation Technologies, Inc., Tucson, Ariz.

[21] Appl. No.: 130,082

[22] Filed: Sep. 30, 1993

[51] Int. Cl.$^6$ .................. G01N 33/49; G01N 33/536; G01N 33/564

[52] U.S. Cl. .................. 435/7.21; 435/2; 435/7.24; 436/172; 436/536; 436/546; 422/82.02; 422/82.08

[58] Field of Search .................. 435/7.21, 2, 7.24, 435/291, 808, 810, 967; 436/536, 546, 172, 800, 805, 808; 422/82.02, 82.08; 356/336

[56] References Cited

U.S. PATENT DOCUMENTS 4,298,836  11/1981  Groves et al. .................. 324/71.1

OTHER PUBLICATIONS

Apple et al., 1991 Detection of Myocardial Reperfusion by Rapid Serial CK–MB or Total CK Assays. Clin. Chem. 37(6): 909–910 (Abstract).

Apple, F. S. 1992 Acute Myocardial Infarction and Coronary Reperfusion. A. J. C. P. 97(2): 217–226. Feb.

Bodor et al., 1992 Development of Monoclonal Antibodies for an Assay of Cardiac Troponin–I and Preliminary Results in Suspected Cases of Myocardial Infarction. Clin. Chem. 38(11): 2203–2214.

Cummins et al., 1987 Cardiac–Specific Troponin–I Radioimmunoassay in the Diagnosis of Acute Myocardial Infarction. Am. Heart J. 113(6): 1333–1344.

Cummins et al., 1987 Comparison of Serum Cardiac Specific Troponin–I with Creatine Kinase, Creatine Kinase–MB Isoenzyme, Tropomyosin, Myoglobin and C–reactive Protein Release in Marathon Runners: Cardiac or Skeletal Muscle Trauma! European J. Clin, Invest. 17: 317–324.

Folts et al., 1976 Platelet Aggregation in Partially Obstructed Vessels and its Elimination with Aspirin. Circulation 54(3): 365–370.

Hendricks et al., 1993 Flow Cytometric Detection and Quantitation of Monocyte–Scientific Sessions, Atlanta, Georgia (Abstract).

Irvin et al., 1980 Acute Myocardial Infarction and MB Creatine Phosphokinase. Arch. Intern. Med. 140: 329–334.

Kanayama et al., 1993 A New Prostacyclin Analog, KP–10614, Inhibits Platelet–Polymorphonuclear Leukocyte Interaction and Limits Experimental Infarct Size in Rat Heart. J. Pharm. and Exper. Therapeutics 266(1): 344–349.

Kaplan et al., 1978 Leukocyte–Platelet Interactions in a Murine Model of Chediak–Higashi Syndrome. Blood 52(4): 719–725.

Katus et al., 1992 Development and In Vitro Characterization of a New Immunoassay of Cardiac Troponin T. Clin. Chem. 38(3): 386–393.

Katus et al., 1991 Diagnostic Efficiency of Troponin T Measurements in Acute Myocardial Infarction. Circulation 83(3): 902–912.

Kline et al., 1986 Three Sera Defining a New Granulocyte––Monocyte–T–Lymphocyte Antigen. Vox. Sang 50: 181–186.

Lee et al., 1986 Serum Enzyme Assays in the Diagnosis of Acute Myocardial Infarction. Annals of Internal Medicine 105: 221–233.

Levine et al., 1976 Leukocyte–Platelet Interaction: Release of Hydrogen Peroxide by Granulocytes as a Modulator of Platelet Reactions. J. Clin. Invest. 57: 955–963.

Lott et al., 1980 Serum Enzymes and Isoenzymes in the Diagnosis and Differential Diagnosis of Myocardial Ischemia and Necrosis. Clin. Chem. 26(9): 1241–1250.

Mehta et al., 1990 Platelet Activation in Unstable Angina: Role of Thromboxane $A_2$ and Other Mediators of Vasocontriction. JACC 15(3): 727–729.

Oda et al., 1986 Polymorphonuclear Leukocyte–Platelet Interactions: Acetylglyceryl Ether Phosphocholine–Induced Platelet Activation under Stimulation with Chemotactic Peptide. J. Biochem. 100(5): 1117–1123.

Puleo et al, 1990 Early Diagnosis of Acute Myocardial Infarction Based on Assay for Subforms of Creatine Kinase–MB. Circulation 82(3): 759–764.

Puleo et al., 1991 Noninvasive Detection of Reperfusion in Acute Myocardial Infarction Based on Plasma Activity of Creatine Kinase MB Subforms. JACC 17(5): 1047–1052.

Rinder et al., 1991 Activated and Unactivated Platelet Adhesion to Monocytes and Neutrophils. Blood 78(7): 1760–1769.

Rinder et al., 1992 Cardiopulmonary Bypass Induces Leukocyte–Platelet Adhesion. Blood 79(5): 1201–1205. Mar.

Rinder et al., 1991 Dynamics of Leukocyte–Platelet Adhesion in Whole Blood. Blood 78(7): 1730–1737.

Roberts, R., 1984 The Two Out of Three Criteria for the Diagnosis of Infarction—Is is Passe! Chest 86(4): 511–513.

Saxena et al. 1993 Quality Assurance Study of Cariac Isoenzyme Utilization in a Large Teaching Hospital. Arch. Pathol. Lab. Med. 117: 180–183. Feb.

Schreiber et al., 1992 Randomized Trial of Thrombolysis Versus Heparin in Unstable Angina. Circulation 86(5): 1407–1414.

(List continued on next page.)

Primary Examiner—Toni R. Scheiner
Assistant Examiner—Nancy J. Parsons
Attorney, Agent, or Firm—Scully, Scott, Murphy & Presser

[57] ABSTRACT

A method and means for detection of an acute myocardial infarcion (AMI) in a patient are provided. The method involves sampling of a patient's peripheral blood, quantifying the level of monocyte platelet conjugates (MP-C) and determining whether a significant increase in monocyte platelet conjugates is present. Quantification can be achieved by direct counting of monocyte platelet conjugates on a slide or under a microscope, by instrumentation measuring apparent monocyte cell volume increases, flow cytometry, or cell counter employing electrical resistance, pulse sizing or light scattering. Diagnostic test kits for detecting an AMI are also provided.

15 Claims, 9 Drawing Sheets

OTHER PUBLICATIONS

Silva et al., 1991 Development and Application of Monoclonal Antibodies to Human Cardiac Myoglobin in a Rapid Fluorescense Immunoassay. Clin. Chem. 37(8): 1356–1364.

Todoroki et al., 1991 Enhancement by IL–1β and IFN–λ of Platelet Activation: Adhesion to Leukocytes Via GMP–140/PADGEM Protein (CD62). Biochem. and Biophys. Res. Comm. 179(2): 756–761.

Tsung et al., 1986 Creatine Kinase Isoenzymes in Extracts of Various Human Skeletal Muscles. Clin. Chem. 32(8): 1568–1570.

Vaananen et al. 1990 Serum Carbonic Anhydrase III and Myoglobin Concentrations in Acute Myocardial Infarction. Clin. Chem. 36(4): 635–638.

Yancy et al., 1989 Analysis of the Interaction of Human C5a and C5a des Arg with Human Monocytes and Neutrophils: Flow Cytometric and Chemotaxis Studies. J. Invest. Dermatol. 92(2): 184–189.

Yee et al., 1986 Intracoronary Platelet Aggregation: Pattern of Deposition after Ischemia, Cardioplegia, and Reperfusion. J. Surgical Res. 40: 499–503.

Zarling et al., 1983 Failure to Diagnose Acute Myocardial Infarction. JAMA 250(9): 1177–1181.

DETECTION OF AN ACUTE MYOCARDIAL INFARCTION IN A PATIENT

The present invention relates to a method and means for the detection and diagnosis of an acute myocardial infarction (AMI) in a patient.

BACKGROUND OF THE INVENTION

Acute myocardial infarction (AMI) continues to be a leading cause of death and disability in the United States. Early detection of AMI is critical for making appropriate therapeutic and triage decisions. Assays which measure increased activity of various serum enzymes have played an important role in detecting AMI. Even so, acute chest pain remains a difficult diagnostic problem as autopsy results indicate many myocardial infarctions go undetected (Lee et al., Ann. Int. Med. 105:221–233, 1986).

The pathophysiologic basis of acute myocardial ischemia (unstable angina pectoris and AMI) has been clearly defined over the past decade. Acute myocardial ischemia is generally thought to be the result of an occlusive thrombus in the atherosclerotic coronary artery. The myocardium may recover from a brief period of ischemia due to a transient and intermittent reduction in coronary blood flow. When the reduction in coronary blood flow is persistent and prolonged, however, an acute myocardial infarction may occur (Mehta, et al., JACC, 15:727–729, 1990).

It is now believed that both unstable angina pectoris (UAP) and AMI are parts of the same pathologic spectrum involving extensive endothelial disruption, activation of platelets at the site of endothelial disruption, and enlargement of the thrombus by incorporation of fibrin and other cellular elements. It is likely that the thrombus is unstable in patients with unstable angina pectoris and stable and firm in patients who develop myocardial necrosis.

Platelets play a central role in hemostasis and in the genesis of arterial thrombosis. Arterial thrombi are composed mainly of aggregated platelets but are also rich in granulocytes (see e.g., Levine, et al., Jor. Clin. Invest. 57: 955–963, 1976). Both monocytes and platelets are known to contribute to myocardial damage following ischemia (Entman et al., FASEB J, 5:2529–2537, 1991; Folts et al., Circulation 54: 365–370, 1976; Yee et al., J. Surg. Res. 40:499–503, 1986).

Coronary endothelial damage and platelet activation are believed to be the pathophysiologic basis of coronary artery occlusion. Activated platelets release potent spasmogens and platelet aggregants, such as thromboxane A2 and serotonin, that exert a vasoconstrictive influence either at the site of thrombus or downstream, beyond the site of arterial occlusion (Mehta, J., JACC 15: 727–729, 1990).

Platelet activation is also associated with surface expression of the α-granule external membrane protein-140 (GMP-140), designated CD62 and also known as platelet activation-dependent granule external membrane protein (PADGEM) or P-selectin. GMP-140 mediates platelet adhesion to polymorphonuclear leucocytes (PMN) and monocytes (Larsen et al., Cell, 59:305, 1989).

Recently, a flow cytometric assay that accurately quantifies platelet-leukocyte adhesion has been developed. The assay accurately measures the percentage of leukocytes binding platelets and the relative number of platelets bound per cell (Rinder et al., Blood, 78:1760–1769, 1991). Using this assay, Rinder et al. have shown that platelet activation on cardiopulmonary bypass (CPB) is temporally accompanied by increased monocyte and PMN adhesion to platelets (Rinder et al., Blood, 79:1201–1205).

AMI has been clinically defined by the World Health Organization (WHO criteria for the diagnosis of acute myocardial infarction; Geneva:Cardiovascular Diseases Unit, 1981). Under the WHO criteria, any two of the following are used for a diagnosis of AMI: (a) typical chest pain, (b) a new Q wave on ECG, and (c) peak enzymes (CK, SCOT or LDH) exceeding two times the upper normal value.

It should be noted, however, that the presence of a new Q wave is rare. Evolution of Q wave abnormalities appear approximately four to eight hours post AMI. Diagnosis of AMI is generally made on chest pain and non-diagnostic changes in the ECG. Typical chest pain is chest pain which radiates down the left arm and into the left hand with a tingling sensation in the fingers.

The cytosolic isoenzyme CK-MB is standard clinical laboratory test used in diagnosing AMI. The serum enzyme creatine kinase (CK) has two subunits, that differ in amino acid sequence and tissue specificity. CK-MB was initially believed to be found only in myocardial cells but more sensitive assays have revealed trace amounts of its presence in other tissues such as normal skeletal muscle. Although increases in CK-MB can occur from non-cardiac sources such as surgery and trauma, elevation in CK-MB in the absence of these factors is highly correlated with myocardial ischemia. (Lee, et al., Ann. Int. Med. 105: 221–223, 1986).

The traditional CK-MB assay requires serial sampling on admission and about twelve and twenty four hours later (Saxena, et al., Arch. Pathol. Lab. Med. 117:180–183). This poses a diagnostic dilemma for emergency physicians because thrombolytic therapy must be initiated within four to six hours after infarction. Because the sensitivity of a single CK-MB determination is low (34%), a single test cannot be used to exclude a diagnosis of AMI. In addition, there may be a significant delay in obtaining the results of CK-MB prior to initiating thrombolytic therapy.

Although it has been suggested that the traditional twenty four hour CK-MB sampling be replaced with two or three very early measurements over a six hour period (Apple et al., Clin. Chem. 37:909, 1991), the time interval between onset of symptoms and appearance of serum CK-MB in clinically significant range varies from 2.8 to 15.1 hours (Irvin et al., Arch. Intern. Med. 140:329–334, 1980). Thus, CK-MB levels determined during the early hours after the onset of symptoms may be negative in a patient who actually has an AMI.

The need for rapid and analytically sensitive assays to replace CK-MB has been an area of great research interest. Many alternatives have been described including assays of CK isoforms (Puelo et al., Clin. Chem. 35:1452–1455, 1989), myoglobin (Drexel et al., Am. Heart J. 105:642–650, 1983), and troponin isoenzymes (Katus et al., J. Mol. Cell Cardiol. 21:1349–1353, 1989). These assays are also based on the appearance of a serum marker of cardiac muscle damage. Similar to the CK-MB assay, the assays must be performed on admission and about twelve and twenty four hours later for a reliable reading. In addition, assay results have at least a one hour turn-around time.

Because of the very different treatment regimes called for in UAP and AMI, early detection of AMI remains an important goal of emergency room care. Thrombolytic therapy is beneficial in AMI if instituted within four to six hours after infarction. It is not beneficial in UAP. Furthermore, thrombolytic therapy is associated with significant risk, e.g., hemorrhage.

It has become apparent that the WHO criteria are nonspecific and do not distinguish transient myocardial ischemia from necrosis. One study has shown that of those patients hospitalized with suspected acute necrosis, only 30% were subsequently confirmed to have AMI (see e.g., Puelo et al., Circulation, 82:759–764 1990).

In addition, more than 50% of the deaths associated with AMI occur within the first two hours after the onset of symptoms of coronary ischemia (Apple, F.S., A.J.C.P.97: 217–226, 1990). Certainly, diagnosis of AMI by CK-MB assay cannot be relied upon during this brief time frame.

Finally, the finding that physicians fail to diagnose myocardial infarctions with alarming frequency (Lee et al., Ann. Int. Med., 105: 221–233) highlights the severe shortcomings still associated with the present state of the art.

Thus, the need is great for a quick and accurate means of identifying an AMI patient from among those patients exhibiting symptoms suggestive of ischemic heart disease.

SUMMARY OF THE INVENTION

The present invention provides a method and means for facilitating diagnosis of an acute myocardial infarction upon its occurrence or at least upon symptomatic manifestation of its occurrence. The invention is based upon the discovery that immediately after an acute myocardial infarction (AMI), there is a significant increase in circulating levels of monocyte platelet conjugates. The term "monocyte-platelet conjugate" or "MP-C" as used in the specification and claims is intended to refer to a monocyte having one or more platelets adhered thereto. Between twenty four and forty eight hours after the occlusive event, platelet-monocyte conjugate levels return to baseline. Accordingly, the method of the present invention should be conducted within such time period.

Surprisingly, monocyte-platelet conjugate levels do not increase in those patients with stable or unstable angina or after severe trauma or infection. Thus, according to the present invention, AMI can be distinguished from other conditions and the appropriate treatment administered to the patient.

The present invention can be achieved by providing a method of diagnosis which includes sampling the peripheral blood of a patient and quantifying the level of monocyte-platelet conjugates (MP-C). The present invention has determined that normally, about 5% of circulating monocytes are conjugated with one or more platelets. Significant MP-C levels above 5%, e.g., two standard deviations from the mean, would signal the occurrence of AMI. An MP-C level of about 10% and above then, would be considered an AMI index.

Quantification of MP-C can be accomplished by any conventional means. For example, quantification of MP-C can be by done by manual counting of adherent events with the aid of a microscope. MP-C levels can also be quantified by flow cytometer.

Because the presence of platelets adhering to monocytes changes the relative cell volume, it is also possible to detect increased levels of monocyte-platelet conjugates using electrical resistance pulse sizing (Coulter sizing; cell counter) or simple light scattering e.g., as with a cell counter.

The present invention also contemplates a number of different AMI diagnostic kits where equipment and reagents needed for an MP-C determination and quantification are provided. The methods used in conjunction with the diagnostic kits are those conventional methods for detecting and quantifying monocyte-platelet conjugates.

More recent methodologies such as flow cytometry of fixed blood samples labeled with antibodies directed to white blood cells and platelets e.g., anti-CD45 and anti-CD41a or determinations of relative volume changes among the monocyte population are also contemplated with the use of different AMI diagnostic kits.

The disclosed invention allows AMI to be either diagnosed or excluded in a patient, thereby distinguishing AMI from other conditions such as stable and unstable angina, severe trauma, or infection. Once AMI is excluded or diagnosed, the proper treatment can be administered.

DETAILED DESCRIPTION OF THE INVENTION

Figure 1A:
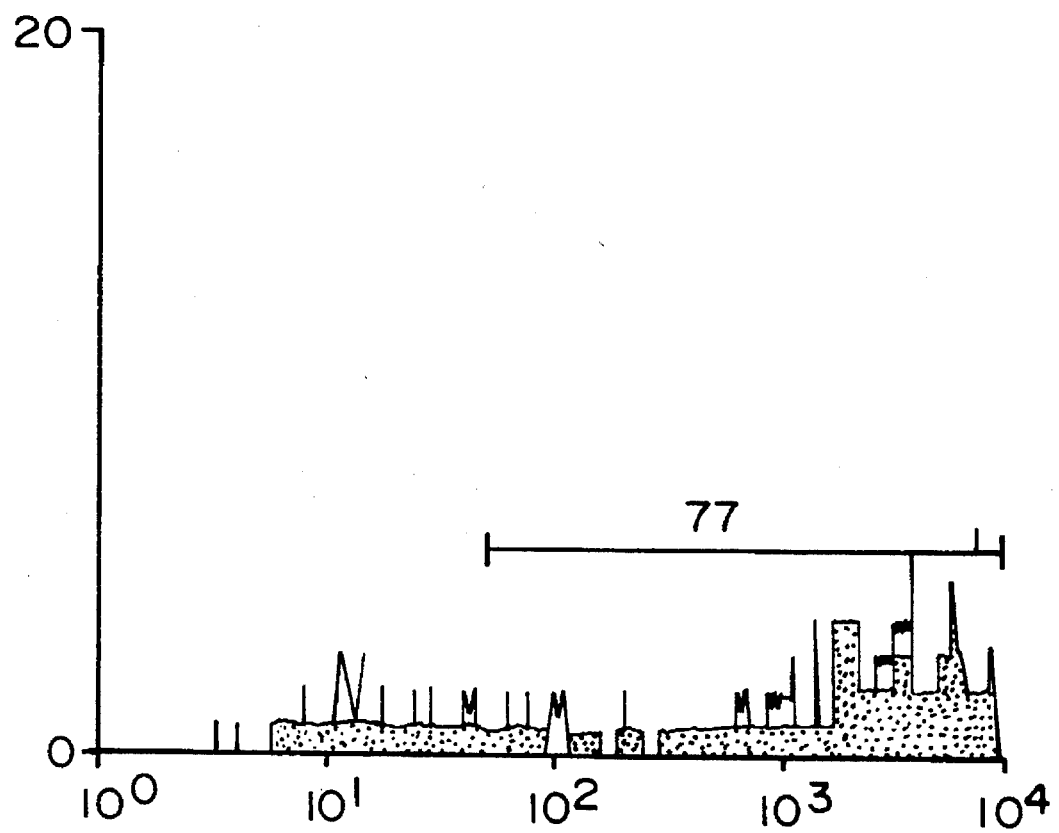
FIG. 1a is flow cytometry histogram data from one representative AMI patient immediately after admission. Percentage of monocyte-platelet conjugates is indicated.

In accordance with the present invention, a patient exhibiting symptoms suggestive of AMI will have his or her blood sampled for a determination of monocyte-platelet conjugate levels. The presence of AMI is determined by comparing the levels of MP-C in a sample of the peripheral blood of the patient to known levels of MP-C associated with AMI. Levels of monocytes bound to platelets and associated with AMI are typically in the 50% range. Since the percentage of monocytes bound to platelets in control blood samples is roughly only 5% significant MP-C levels above 5%, for example two standard deviations from the control mean would signal the presence of an AMI. A level of 10% and above then, would be considered an AMI index. Once an MP-C conjugate level is determined, decisions regarding the appropriate treatment can be rationally made.

In accordance with the present invention, a monocyte-platelet conjugate reading is taken from a patient with clinical symptoms of AMI. The primary symptom of kMI includes chest pain which radiates down the left arm and into the left hand with a tingling sensation in the fingers.

Also in accordance with the present invention, a monocyte-platelet conjugate reading is taken whenever an AMI is a possibility, for example, in a semi-conscious or unconscious patient.

In a preferred embodiment, the blood samples are taken by veinipuncture, typically in the arm. Blood is collected into a tube containing a fixative and anticoagulant. Any combination of fixative and anticoagulant commonly used in the clinical laboratory is employed. Examples of fixatives which can be used are 10% buffered formalin/formaldehyde, glutaraldehyde, or paraformaldehyde. Anticoagulants which can be used include sodium citrate, sodium oxalate, heparin, and heparin-like compounds. The fixative and anticoagulant serve to prevent the spurious formation of monocyte-platelet conjugates which may arise as a result of platelet activation associated with veinipuncture.

In another preferred embodiment, the collecting tube contains a volume of 2% paraformaldehyde and 3.8% sodium citrate in phosphate buffered saline (PBS) to bring the paraformaldehyde final concentration to between 1–5%. Samples must not be allowed to remain in fixative longer than six hours. As little as ten minutes is sufficient fixing time.

In the case of direct manual counting of MP-C, a few drops of fixed blood is placed on a slide, stained by standard procedure, and a cover slip applied. Monocyte platelet conjugate numbers are determined by counting at least two hundred monocytes and then reporting the percentage of monocytes with one or more platelets adhered. This method is used in situations when a flow cytometer or cell sizing instrument, e.g., cell counter, is not available.

Another method of determining monocyte-platelet conjugate levels is by detecting changes in volume/cell surface area. In this embodiment of the invention, the percentage of cell adherent events with a volume consistent with MP-C is recorded. If the relative number of MP-C falls outside of normal range, AMI is suggested.

Another preferred method of obtaining an MP-C reading is by flow cytometric assay. Saturating concentrations of an antibody directed against white blood cells and an antibody directed against platelets are employed along with the appropriate isotype control agents. Examples of antibodies directed against white blood cells include CD13, CD14, and CD45. Examples of antibodies directed against platelets are CD41a, CD41b, and CD42a. Examples of the appropriate labeled isotype control are IgG1 antibodies prepared from the same animal but to an irrelevant antigen.

The antibodies used in the preferred embodiment are linked to a "reporter molecule". The term "reporter molecule" as used in the present specification and claims, refers to a molecule, which, by its chemical nature, provides an analytically identifiable signal which allows the detection of antigen-bound antibody. Detection may be either qualitative or quantitative. Common reporter molecules are enzymes, flurophores or radionucleotides-containing molecules.

In the preferred embodiment of the invention, a small sample of the paraformaldehyde fixed blood is placed in two separate tubes and washed two times with isotonic saline buffer. Saturating concentrations of fluorescein isothiocyanate (FITC) conjugated anti-CD45 is added to both tubes. Biotinylated anti-GPIIb/IIIa (CD41a) is added to one tube and the appropriate labeled isotype control to the other. Examples of the appropriate labeled isotype control are IgG1 antibodies prepared from the same animal but to an irrelevant antigen. The tubes are then incubated for fifteen minutes at 4° C., washed and resuspended in two hundred microliters of an isotonic buffer such as PBS for analysis by flow cytometry.

In a further embodiment, the present invention also contemplates a diagnostic kit for the detection of AMI. The kit contains equipment and reagents to be used in detecting and quantifying monocyte-platelet conjugates in a sample of a patient's blood. A kit for use with a flow cytometry or cell counter is compartmentalized to receive a first container adapted to contain an antibody having specificity for white blood cells and linked to a labeled reporter molecule. A second container is adapted to contain an antibody having specificity for platelets and also linked to a reporter molecule. Vacuum stoppered vials containing pre-measured fixative and anticoagulent are also provided.

The preferred diagnostic test kit for use with flow cytometry is compartmentalized to receive a first container adapted to contain FITC-conjugated anti-CD45 and biotinylated anti GPIIb/IIIa (CD41a) and a second container adapted to contain avidin conjugated phycoerythrin label (PE avidin). Vacuume stoppered vials containing pre-measured fixative and anticoagulant are also provided.

The present invention is further illustrated by the following specific examples which are not intended in any way to limit the scope of the invention.

EXAMPLE 1

Monocyte-Platelet Conjugates as a Marker of Coronary Damage and AMI

A flow cytometric assay to determine the percentage of leukocyte subsets with bound platelets in whole blood was performed. Forty one blood samples from twenty eight patients with coronary artery disease (CAD) and four control subjects were obtained. Seven milliliters (ml) of blood was collected into a Vacutainer. The samples were immediately fixed in 2% paraformaldehyde, 3.8% sodium citrate in PBS to bring the total concentration of paraformaldehyde to 1% for flow cytometry.

Flow cytometry was performed according to a modification of the procedure of Rinder et al. One hundred microliter (μl) aliquots of paraformaldehde fixed peripheral blood was placed in each of two tubes and washed two times with PBS. A saturating concentration of FITC conjugated anti-CD45 (Becton-Dickinson Immunocytometry Systems, San Jose, Calif.) was added to both tubes. Biotinylated anti-GPIIb/IIIa (CD41a; AMAC, INC., Westbrook, Me.) was added to one tube and biotinylated IgG1 (isotype control) to the other. Tubes were incubated for fifteen minutes at 4° C., followed by washing and resuspension in PBS. The samples were then incubated with saturating concentrations of phycoerythrin-avidin (PE-avidin) (Becton Dickinson) for 15 minutes at 4° C., washed and resuspended in 200 μl PBS for flow cytometry analysis.

Figure 2:
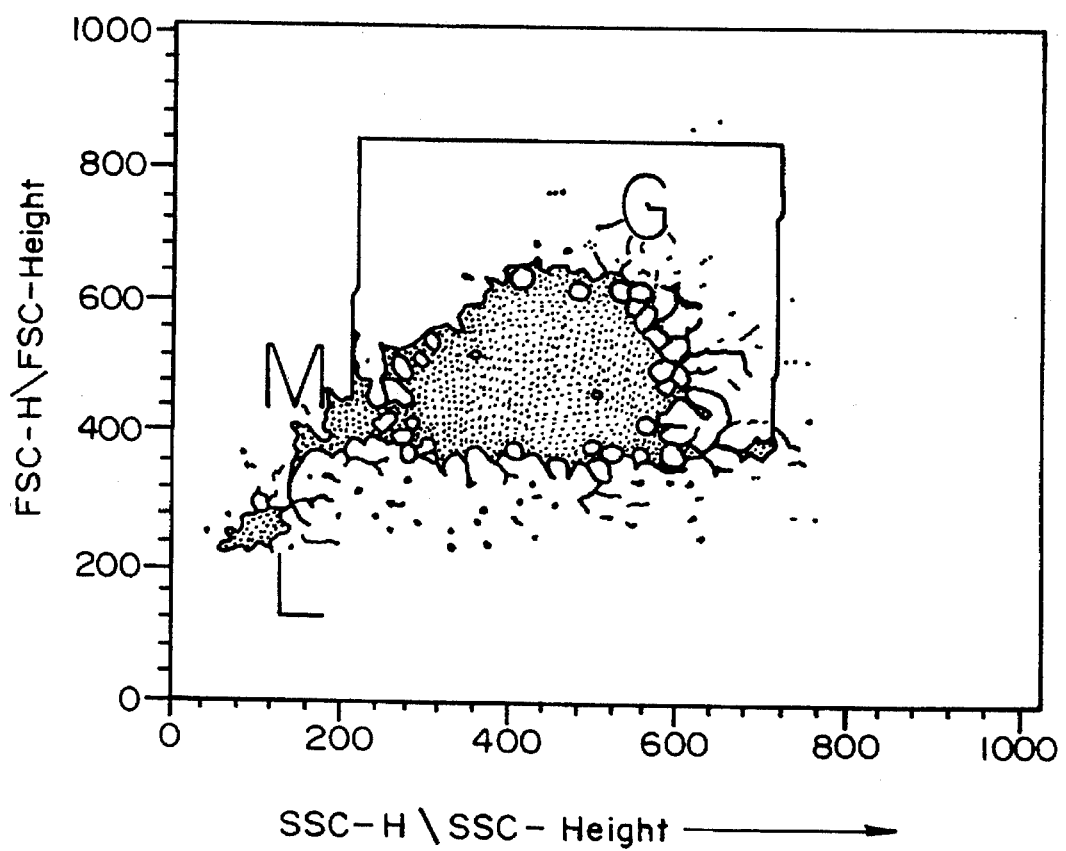
FIG. 2 is a forward scatter (size parameter (y axis)) versus side scatter (complexity parameter (x axis)) plot of blood leukocytes showing clear delineation between lymphocytes (L), monocytes (M) and granulocytes (PMN).
Figure 3A:
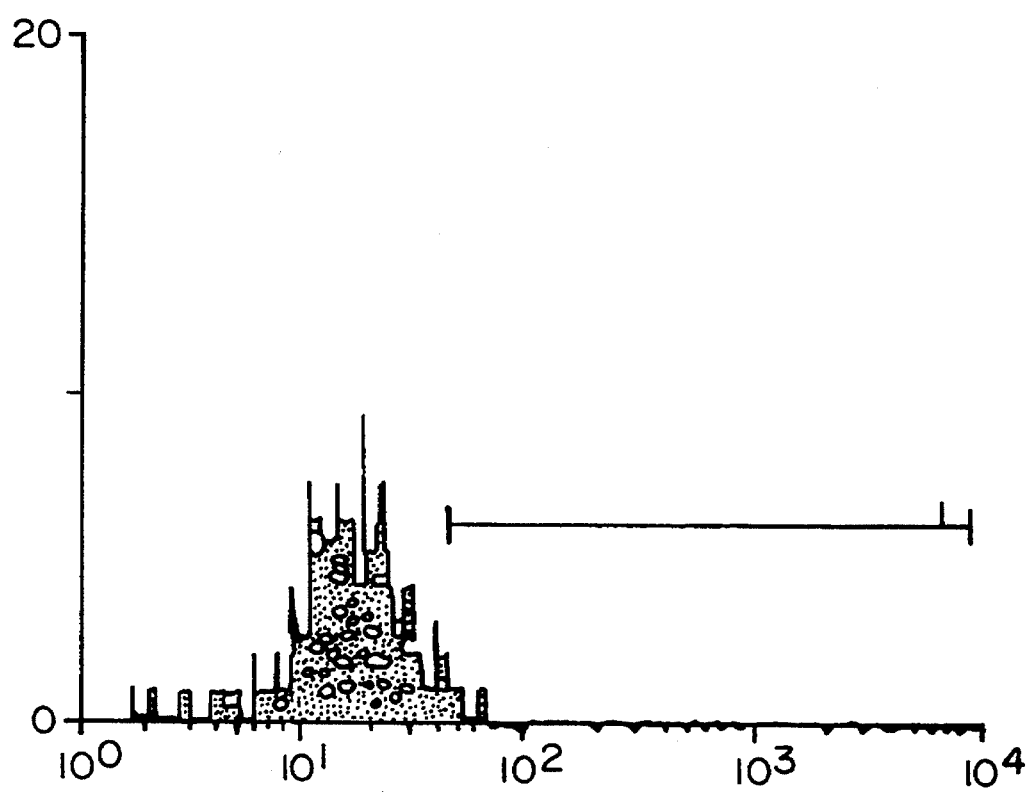
FIG. 3a is a histogram showing fluorescence from an isotype control antibody used to control for non specific immunostaining. This is used to establish a threshold for positive platelet events.
Figure 3B:
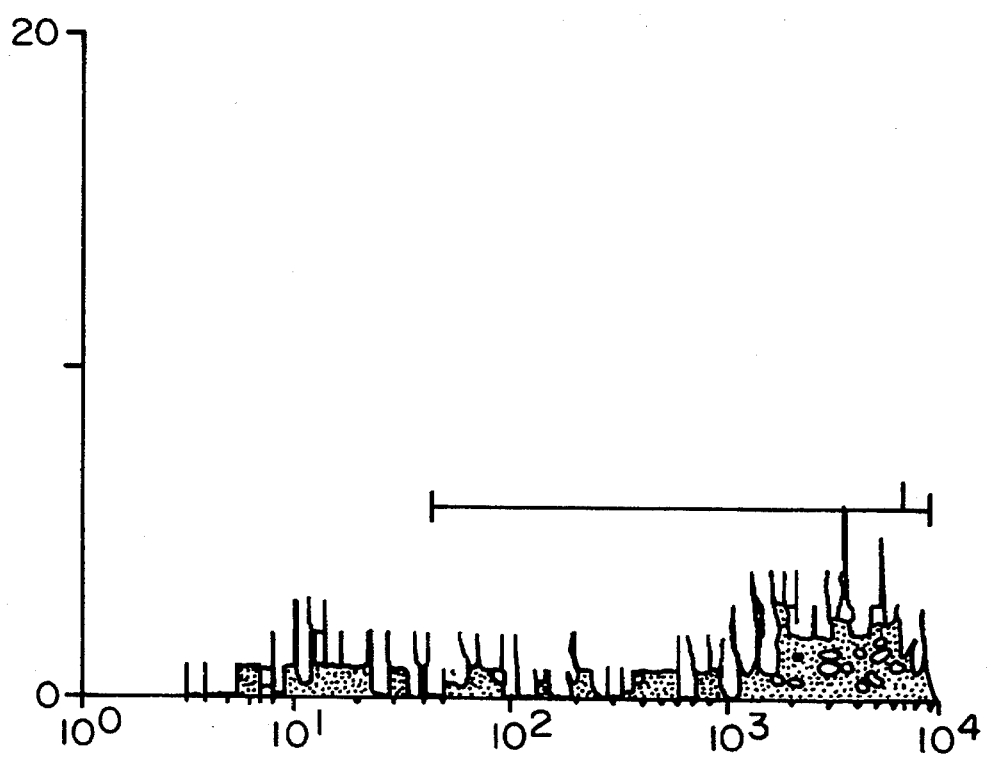
FIG. 3b is a histogram showing CD41a (anti-GPIIb/IIIa) fluorescence gated from the monocyte region of blood collected from an AMI patient on admission. The percentage of platelet positive events exhibiting greater fluorescence than the maximum channel of control fluorescence is recorded.

Samples were analyzed on a FACScan flow cytometer (Becton-Dickinson) with data stored in list mode. The instrument threshold was set on FL1 (FITC fluorescence). This adjustment sets a lower level discrimination on the CD45-FITC signal (WBC's) so that the instrument ignores signals that do not exceed the threshold setting. This provides a convenient method for ignoring the red blood cells which are present in the sample and are not to be analyzed. Using a combination of forward and side scatter, the monocyte and PMN regions can be located for purposes of electronic gating (FIG. 2). Events falling within the gated region were analyzed for the presence of CD41a-PE ("red fluorescence"). The tube containing the isotype control antibody was used to set a threshold (98% of events below the threshold) for positive platelet fluorescence (CD41a-PE). The percentage of platelet positive conjugates was recorded for both monocyte and PMN populations (FIG. 3b). Previous studies have demonstrated that this flow cytometry assay can detect leukocytes with only a single bound platelet (Rinder et al., Blood 78:1730–1737, 1991).

Using a flow cytometric assay to determine the percentage or leukocyte subsets with bound platelets in whole blood, blood from twenty eight patients with coronary artery disease and eight controls were examined. As shown in Table 1, monocyte-platelet conjugates (M-PC) increases several fold in the early hours of AMI ($p<0.05$) relative to controls. The number of M-PC returned to baseline levels within forty eight hours post AMI. No increase in M-PC was observed for patients with stable or unstable angina.

TABLE I

| Diagnosis | M-P Conjugates (% of monocytes) |
| --- | --- |
| Normal controls (n = 4) | 6.50 ± .19 |
| Stable Angina (n = 7) | 5.85 ± 1.47 |
| Acute MI (n = 4) | 52.25 ± 15.81* |
| >24 hours post MI (n = 5) | 9.80 ± 4.06 |
| Stable CAD pre-PTCA (n = 7) | 5.12 ± 1.18 |
| 10 minutes post-PTCA (n = 7) | 7.20 ± 5.34* |
| >1 hour post-PTCA (n = 7) | 5.28 ± 1.08 |

*$P<0.05$ versus control

It is noteworthy that the MP-C levels were in the normal range in unstable angina pectoris (UAP), even though both the symptomatic and pathologic basis of UAP is similar to that of AMI. UAP is usually defined by a change in the pattern of chest pain such as a recent increase in severity, frequency, or both. The only difference between the two states relates to persistence of thrombus in AMI and spontaneous dissolution of thrombus in UAP. The M-PC data in UAP and AMI demonstrate a relatively high degree of platelet activation in AMI and only a transient activation in UAP which cannot be detected in peripheral blood.

Figure 1B:
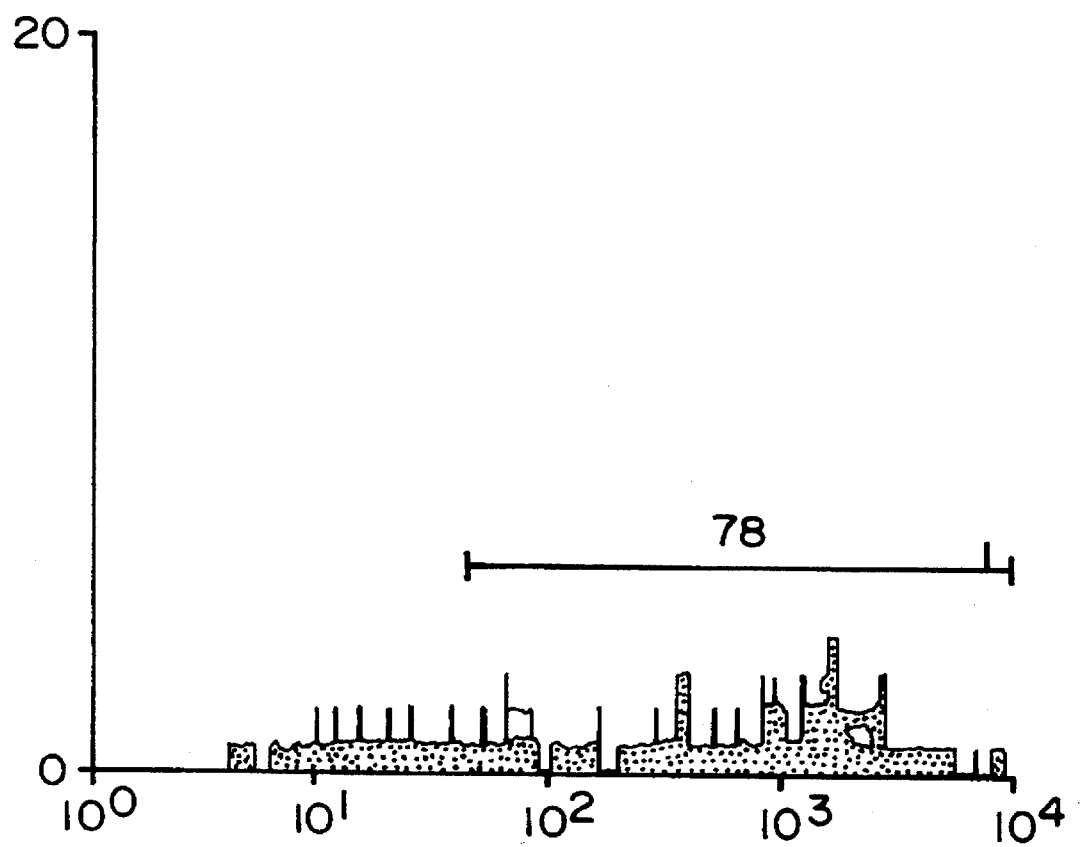
FIG. 1b is flow cytometry histogram data from the same patient two hours after administering streptokinase.
Figure 1C:
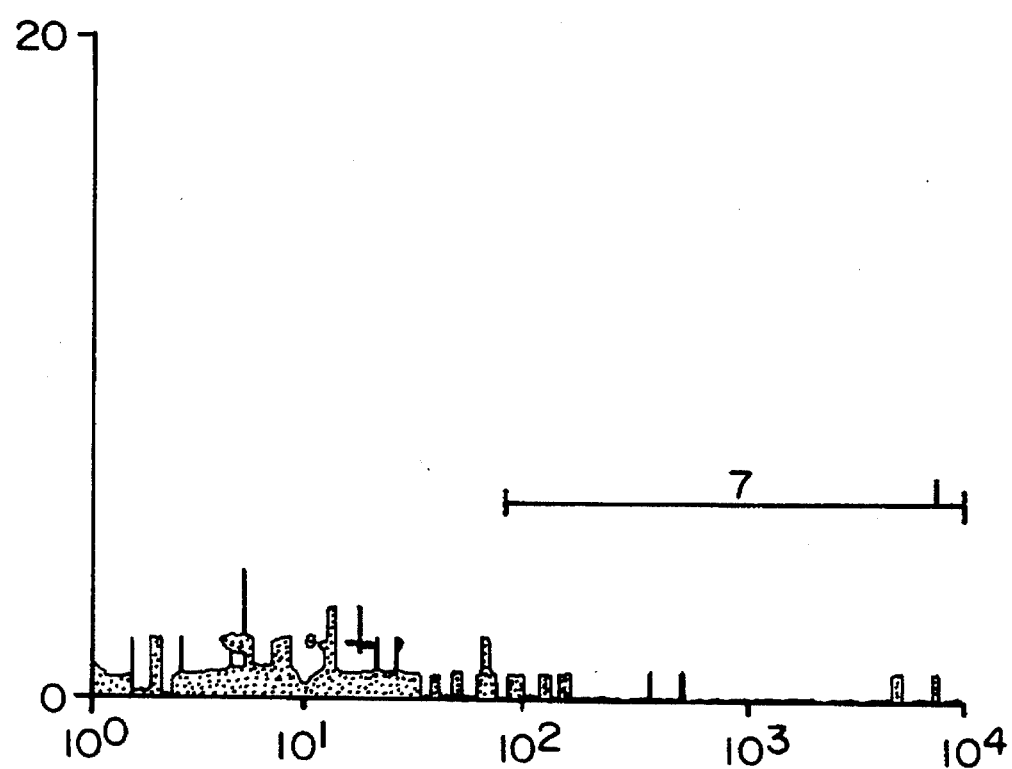
FIG. 1c is flow cytometry histogram data from the same patient 4 days later.

FIGS. 1a–1c show flow cytometry histogram data from one representative AMI patient. The number of M-PC was high on admission to the emergency room (A) and two hours after the administration of streptokinase (B), but had returned to baseline levels four days later (C). The histograms were generated by gating on the monocyte fraction, and analyzing CD41a (platelet GPIIb/IIIa) fluorescence. The cursor position was established by analysis of an isotype matched control. The percentage of CD41a positive events represents the percentage of monocytes with at least one bound platelet. (Rinder et al., Blood, 78: 1730–1737, 1991.)

Marked elevation of M-PC in AMI patients demonstrates intense platelet and monocyte activation far greater than in patients with other forms of ischemic heart disease.

EXAMPLE 2

Monocyte-Platelet Level Studies in Percutaneous Transluminal Coronary Angioplasty (PCTA)

Figure 4:
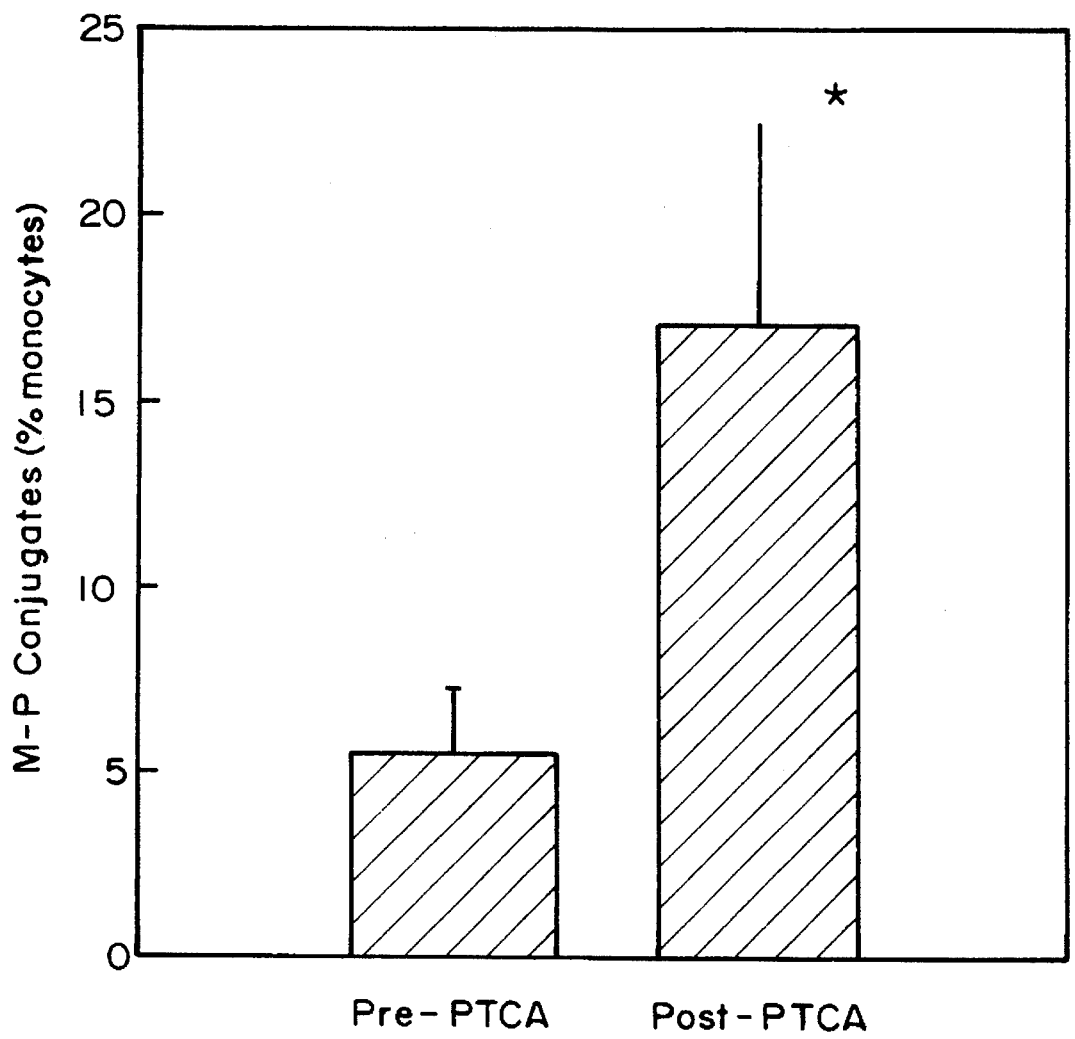
FIG. 4 is a graph showing the percentage of monocyte-platelet conjugates before and after Percutaneous Transluminal Coronary Angioplasty (PCTA).

To establish a relationship between coronary endothelial cell damage and platelet activation, the percentage of M-PC in five patients before and ten minutes post percutaneous transluminal coronary angioplasty (PTCA) was examined by flow cytometry as described in Example 1. As FIG. 4 demonstrates, a significant increase ($p<0.05$) in the percentage of monocyte-platelet conjugates was observed immediately following PTCA. The pre-PTC M-PC value was within the normal range (5.6±1.69). Ten minutes post-PTCA, however, an average of 17.2±5.34 M-PC were detected. M-PC levels returned to baseline by one hour post-PTCA (Table 1). The relative number of M-PC conjugates in the peripheral blood post-PTCA was below the levels observed for patients with AMI.

These observations suggest that the magnitude of endothelial injury, platelet activation and M-PC formation is less following balloon-induced vascular injury than in naturally occurring coronary artery thrombosis leading to AMI.

These data provide convincing evidence that the levels of M-PC in peripheral venous blood may be used for the early detection on AMI and that an increase in M-PC levels over baseline accompanies coronary endothelial cell damage and presumable platelet activation. The fact that M-PC levels were not high in unstable angina suggests that the extent and severity of endothelial damage or the stability of the thrombus may be important considerations. M-PC conjugates persist in the peripheral blood for a period of approximately twenty four to forty eight hours post AMI and one hour post PCTA.

Only modest and transient rise in M-PC levels in patients undergoing PTCA suggest that the degree of platelet-leukocyte activation is not of the same magnitude as in AMI. M-PC then, will provide an important tool for diagnosis of AMI and also provide an index of coronary arterial endothelial injury and platelet activation.

EXAMPLE 3

Circulating ICAM-1 as a Marker of Coronary Endothelial Damage and AMI

Numerous studies in animals demonstrate that neutrophils play an important role in the pathophysiology of myocardial ischemia and infarction. In the search for early events that might serve as diagnostic and therapeutic targets, studies were conducted with intra-cellular adhesion molecule (ICAM-1) which is a molecule that mediates leukocyte-endothelial adhesion.

Figure 5:
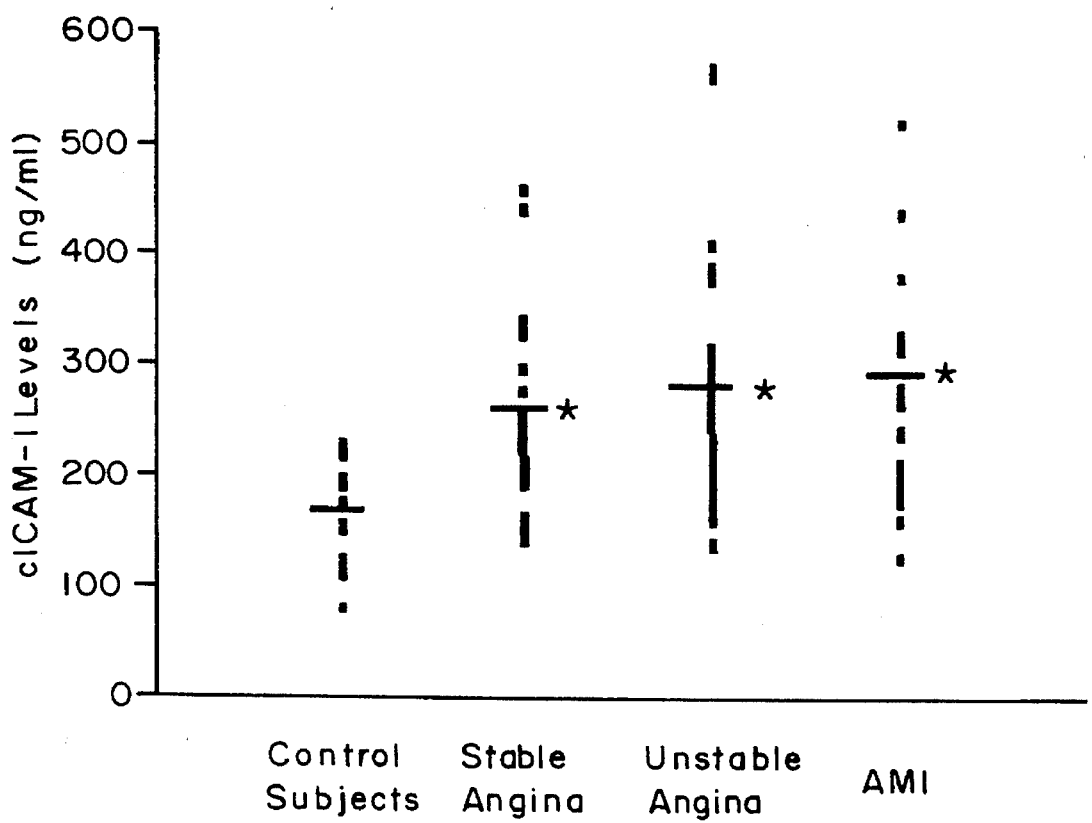
FIG. 5 is a graph showing cICAM-1 levels in patients having ischemic heart disease (stable and unstable angina pectoris and AMI).

It has been suggested that ICAM-1 is upregulated on endothelium following occlusion/reperfusion. Since shedding of adhesion molecules represents a potential method of modulating and controlling adhesion, it was hypothesized that the levels of circulating adhesion molecules in serum might be used as an early marker of coronary endothelial cell damage and AMI. Serum from eighty seven patients with ischemic heart disease and sixteen controls were examined for the presence of circulating ICAM-1 (cICAM-1) by enzyme linked immunosorbant assay (ELISA) following the instructions of the manufacturer. A significant increase in cICAM-1 levels was observed for patients with stable angina pectoris (N=30; $p<0.05$), unstable angina pectoris (N=39; $p<0.05$), and AMI (N=18; $p<0.05$) relative to controls (FIG. 5). These results demonstrate that cICAM-1 cannot be used as an effective marker for AMI.

Figure 6:
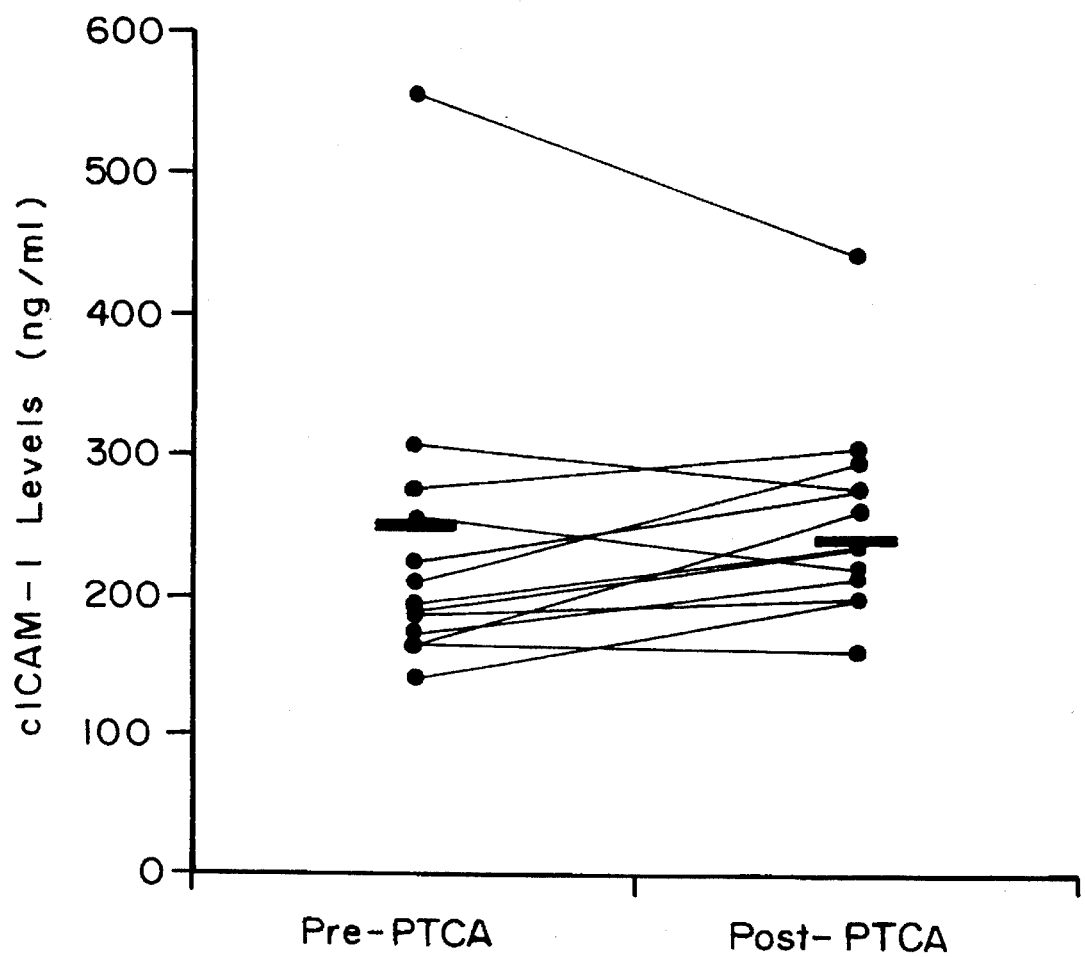
FIG. 6 is a graph showing cICAM-1 levels in patients before and after PTCA.

The relationship of cICAM-1 with coronary endothelial damage was examined by examining cICAM-1 levels from twelve patients prior to and at ten minutes after percutaneous transluminal coronary angioplasty (PTCA). If the increase in cICAM-1 levels observed in ischemic heart disease is directly related to coronary endothelial cell damage, an increase in cICAM-1 over basal levels should be induced by PTCA. No significant increase in cICAM-1 levels was observed however, following PTCA (FIG. 6). These data suggest that the increase in cICAM-1 levels in ischemic endothelium in ischemic heart disease is in a constant state of activation.

EXAMPLE 4

Monocyte-platelet Conjugate Level Determinations by Direct Manual Counting on Microscope Slide In this method, a blood smear is prepared from the paraformaldehyde fixed blood sample. A small drop of blood sample is placed on a microscope slide, smeared, dried, and fixed with methanol. The slide is stained in Wright's stain or other type of Romanowsky stain and a cover slip applied. At least two hundred monocytes are identified by morphology and monocytes with one or more platelets adhered are counted and recorded. An MPC level of about 10% or greater is used as an index of AMI.

EXAMPLE 5

Monocyte-platelet Conjugate Level Determinations by Electrical Resistance Pulse Sizing or Light Scattering A small sample from the original seven ml fixed blood sample is drawn up into a cell counter, for example a conventional flow cytometer or flow cytometer equipped for electrical sizing. The instrument, is programmed to identify cell adherent events consistent with that of MP-C. An MPC level of 10% or greater is used as an index of AMI.

EXAMPLE 6

Diagnostic Test Kit for Detecting AMI Using Flow Cytometry

A test kit for determining MP-C levels using a flow cytometric assay contains vacuum stoppered vials containing pre-measured paraformaldehyde and sodium citrate. FITC-conjugated anti-CD45 and biotinylated anti-GPIIb/IIIa (CD41a) is contained in another vial or tube. Avidin conjugated phycoerythrin label is provided in another vial or tube. A positive AMI blood sample and negative AMI blood sample is also provided The procedure described in Example 1 is followed.

EXAMPLE 7

Diagnostic Test Kit for Detecting AMI by Apparent Monocyte Cell Volume Increases A third test kit for determining MP-C levels contains vacuum stoppered tubes containing fixative and anticoagulant in pre-measured amounts. A positive AMI blood sample and a negative AMI blood sample is also included in the kit.

It is to be understood that the above examples are illustrative of the present invention and are not meant to limit the scope thereof.

What is claimed is:

1. A method of detecting the occurrence of an acute myocardial infarction (AMI) in a patient which comprises obtaining a sample of blood from the patient, quantifying monocyte-platelet conjugates in the sample, comparing the level of monocyte-platelet conjugates in the sample to a standard level of circulating monocyte-platelet conjugates and correlating an increase in monocyte-platelet conjugates in the sample with the occurrence of an AMI.

2. A method according to claim 1 wherein said quantifying is performed by manual counting of the monocyte-platelet conjugates on a slide under a microscope.

3. A method according to claim 1 wherein said quantifying is performed by flow cytometry.

4. A method according to claim 1 wherein said quantifying is performed by means of a cell counter.

5. A method according to claim 1 wherein said quantifying is performed by means of a cell counter employing electrical resistance pulse sizing.

6. A method according to claim 1 wherein said quantifying is performed by means of a cell counter employing light scattering.

7. The method of claim 1 wherein the step of quantifying comprises:

a) immediately fixing the blood sample in approximately 2% paraformaldehyde and approximately 3.8% sodium citrate;

b) incubating the fixed blood sample with (FITC)-anti-CD45 and biotinylated anti-GPIIb/IIIa (CD41a);

c) incubating the blood sample with saturating concentrations of PE-avidin;

d) washing and resuspending the reacted blood sample; and e) quantifying the monocyte-platelet conjugates in the blood sample.

8. The method of claim 7 in which step (e) is performed by a flow cytometer.

9. The method of claim 7 in which step (e) is performed by an instrument which measures apparent cell volume.

10. The method of claim 7 in which step (e) is performed by a cell counter employing electrical resistance pulse sizing.

11. The method of claim 7 in which step (e) is performed by a cell counter employing light scattering.

12. The method according to claim 1 wherein the increase is defined by a monocyte-platelet conjugate level two standard deviations from the normal mean level of circulating monocyte-platelet conjugates.

13. The method according to claim 1 wherein the increase is defined by about 10% or greater monocyte-platelet conjugates in the sample.

14. A method according to claim 1 wherein said quantifying is performed by means of a fluorescence based cell counter.

15. The method of claim 7 in which step (e) is performed by a fluorescence based cell counter.

* * * * *

UNITED STATES PATENT AND TRADEMARK OFFICE
CERTIFICATE OF CORRECTION

PATENT NO. : 5,503,982
DATED : April 2, 1996
INVENTOR(S) : James B. Hendricks, et al It is certified that error appears in the above-indentified patent and that said Letters Patent is hereby corrected as shown below:

On the title page: Section [56], under "OTHER PUBLICATIONS" delete [ Hendricks et al., 1993 Flow Cytometric Detection and Quantitation of Monocyte-Scientific Sessions, Atlanta, Georgia (Abstract)].

Column 1, line 21, "Trauma!" should read -- Trauma? --.
Column 2, line 36, "is is Passe!" should read -- Is is Passe?--.
Column 5, line 3, "kMI" should read --AMI--.

Signed and Sealed this

Fourteenth Day of October, 1997

Attest:

BRUCE LEHMAN

Attesting Officer

Commissioner of Patents and Trademarks